United States Patent
White et al.

(10) Patent No.: US 10,807,934 B1
(45) Date of Patent: Oct. 20, 2020

(54) HIGH LINEAR SELECTIVITY LIGAND FOR ALLYL ALCOHOL HYDROFORMYLATION

(71) Applicant: Lyondell Chemical Technology, L.P., Houston, TX (US)

(72) Inventors: Daniel F. White, Houston, TX (US); Beaven S. Mandimutsira, Sugar Land, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 16/881,864

(22) Filed: May 22, 2020

Related U.S. Application Data

(60) Provisional application No. 62/855,254, filed on May 31, 2019.

(51) Int. Cl.
| | | |
|---|---|---|
| *C07C 45/50* | (2006.01) | |
| *B01J 23/46* | (2006.01) | |
| *C07F 9/28* | (2006.01) | |
| *C07C 47/19* | (2006.01) | |

(52) U.S. Cl.
CPC ........... *C07C 45/505* (2013.01); *B01J 23/464* (2013.01); *C07F 9/28* (2013.01); *C07C 47/19* (2013.01)

(58) Field of Classification Search
CPC ......... C07C 45/505; C07C 47/19; C07F 9/28; B01J 23/464
See application file for complete search history.

(56) References Cited

U.S. PATENT DOCUMENTS

| | | | |
|---|---|---|---|
| 7,279,606 B1 | 10/2007 | White | |
| 2014/0005440 A1* | 1/2014 | Mandimutsira | ......... C07C 45/50 568/454 |
| 2014/0243558 A1 | 8/2014 | Arlt | |

FOREIGN PATENT DOCUMENTS

WO  2012163831 A1  12/2012

OTHER PUBLICATIONS

The International Search Report the The Written Opinion for PCT/US2020/034304 dated Jul. 13, 2020.

* cited by examiner

*Primary Examiner* — Jafar F Parsa

(57) ABSTRACT

A process for selectively producing 4-hydroxybutyraldehyde from allyl alcohol is described. The process comprises reacting allyl alcohol with a mixture of carbon monoxide and hydrogen in the presence of a solvent and a catalyst system comprising a rhodium complex and a trans-1,2-bis(bis(3,4,5-tri-n-alkylphenyl)phosphinomethyl)-cyclobutane. The process gives high yield of 4-hydroxybutyraldehyde compared to temperature.

20 Claims, 1 Drawing Sheet

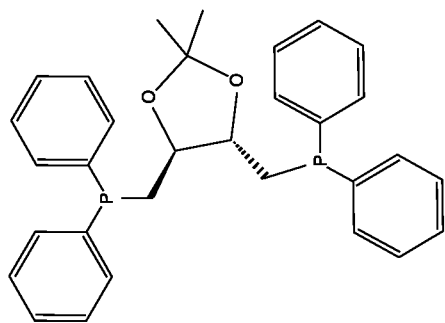
Diop (1D)
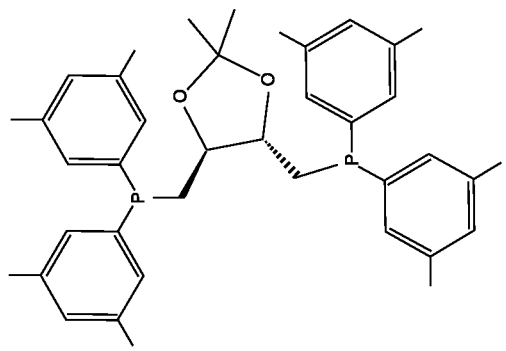
Ligand A3 (1C)
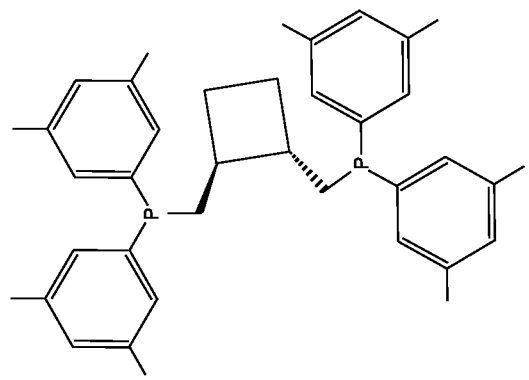
Ligand A2 (1B)
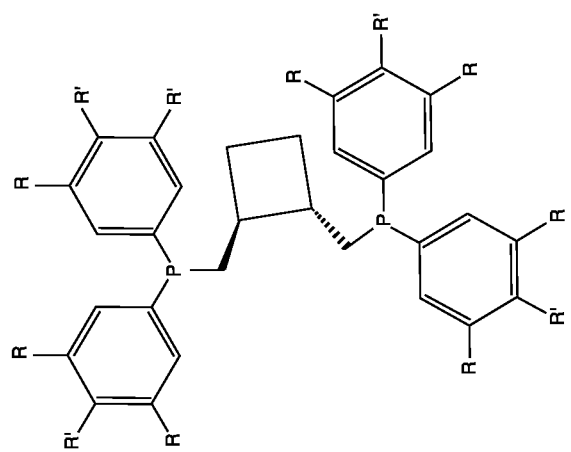
Ligand A1 (1A)

HIGH LINEAR SELECTIVITY LIGAND FOR ALLYL ALCOHOL HYDROFORMYLATION

PRIOR RELATED APPLICATIONS

This application claims the benefit of priority to U.S. Provisional Application No. 62/855,254 filed May 31, 2019, which is incorporated here by reference in its entirety.

FIELD OF THE DISCLOSURE

In general, the present disclosure relates to the field of chemistry. More specifically, the present disclosure relates to allyl alcohol hydroformylation. In particular, the present disclosure relates to a ligand for use in the allyl alcohol hydroformylation stage of the 1,4-butanediol production process.

BACKGROUND OF THE DISCLOSURE

The hydroformylation of allyl alcohol is a well-known and commercially practiced process. In the hydroformylation reaction, allyl alcohol is reacted with a $CO/H_2$ gas mixture in the presence of a catalyst to form 4-hydroxybutyraldehyde (HBA). The HBA may then be separated from the catalyst, e.g., by water extraction, and hydrogenated to form 1,4-butanediol (BDO).

Various catalyst systems have been employed for the hydroformylation reaction, most notably a rhodium complex together with a phosphine ligand. Commonly employed phosphine ligands are trisubstituted phosphines such as triphenyl phosphine. One disadvantage of the hydroformylation process is that other co-products or byproducts are also formed in addition to the desired HBA linear product. The hydroformylation of allyl alcohol typically produces some 3-hydroxy-2-methylpropionaldehyde (HMPA) branched co-product and $C_3$ byproducts such as n-propanol and propionaldehyde. Although HMPA may be hydrogenated to produce 1,3-methyl propanediol (MPD), which is a useful material, the MPD co-product reduces the yield of BDO. Formation of the $C_3$ byproducts effectively represents another yield loss in the process which can have a severe adverse effect on the process economics.

To increase BDO yields, research continues to improve the hydroformylation process and reduce less desired co-product/byproducts. The use of a trialkyl phosphine ligand having at least 2 methyl groups has been found to increase HBA:HMPA ratio. The use of disphosphine ligands has also been found to improve the HBA:HMPA ratio. The hydroformylation of allyl alcohol may use rhodium complex catalysts and disphosphine ligands such as DIOP or trans-1,2-bis(diphenyl-phosphinomethyl)cyclobutane.

Hydroformylation is a technique for producing 1,4-butanediol (BDO) from allyl alcohol (AA) with a $CO/H_2$ mixture in the presence of a catalyst. Different ligands have been used to improve the production, especially increasing the ratio of 4-hydroxybutyraldehyde (HBA) to its branched co-product 3-hydroxy-2-methyl propanal (HMPA). Linear HBA is preferable to the branched HMPA due to its easier synthesis pathway to the final BDO product. Currently the use of Ligand A2 (trans-1,2-bis(bis(3,5-dimethylphenyl) phosphinomethyl)cyclobutane) has a linear-to-branch ratio of 10, and BDO yield at approximately 90%.

SUMMARY OF THE DISCLOSURE

The present disclosure is directed to a process of making 1,4-butanediol using trans-1,2-bis(bis(3,4,5-tri-n-alkyl-phenyl)phosphinomethyl)cyclobutane (Ligand A1) in order to improve the overall yield, and especially to improve the HBA:HMPA ratio to 11 or higher. The process comprises reacting allyl alcohol with carbon monoxide and hydrogen in the presence of a solvent and a catalyst system to produce HBA. The catalyst system comprises a rhodium complex and a trans-1,2-bis(bis(3,4,5-tri-n-alkyl-phenyl)phosphinomethyl) cyclobutane. Trans-1,2-bis(bis(3,4,5-tri-n-alkyl-phenyl)phosphinomethyl) cyclobutane has the structure:

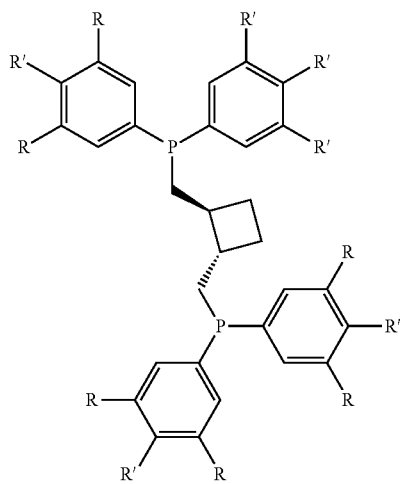

wherein each of R and R' is an n-alkyl or substituted n-alkyl group. In some embodiments, each of R and R' is independently selected from methyl, ethyl, propyl, fluorinated methyl, fluorinated ethyl, or fluorinated propyl.

The present disclosure also discloses a disphosphine ligand of trans-1,2-bis(bis(3,4,5-trimethylphenyl)phosphinomethyl)cyclobutane or trans-1,2-bis(bis(3,4,5-triethylphenyl)phosphinomethyl)cyclobutane. The methyl or ethyl group can further be fluorinated, for example, a fluoromethyl, a difluoromethyl, or a trifluoromethyl group.

The trans-1,2-bis(bis(3,4,5-tri-n-alkyl-phenyl)phosphinomethyl)cyclobutane may be prepared by any possible method. For instance, it may be prepared by the reaction of trans-1,2-cyclobutanedimethanol, bis(toluenesulfonate) with lithium di(3,4,5-tri-n-alkylphenyl)phosphine.

The disclosure also provides a process to produce 4-hydroxybutyraldehyde by reacting allyl alcohol with carbon monoxide and hydrogen in the presence of a solvent and a catalyst system that includes a rhodium complex and a trans-1,2-bis(3,4,5-tri-n-alkylphenylphosphinomethyl)cyclobutane.

In some embodiments of the disclosure, the catalyst system comprises the rhodium complex and trans-1,2-bis (bis(3,4,5-trimethylphenyl)phosphinomethyl)cyclobutane. In some embodiments of the disclosure, the catalyst system comprises the rhodium complex and trans-1,2-bis(bis(3,4,5-triethylphenyl)phosphinomethyl)cyclobutane.

In some embodiments of the disclosure, the solvent may be selected from the group consisting of $C_5$-$C_{20}$ aliphatic hydrocarbons, $C_6$-$C_{12}$ aromatic hydrocarbons, ethers, alcohols, and mixtures thereof. In some embodiments of the disclosure, the solvent may be selected from the group consisting of toluene, methyl-cyclohexane, cyclohexane, methyl t-butyl ether, and mixtures thereof.

In some embodiments of the disclosure, the rhodium complex comprises rhodium and ligands selected from the group consisting of hydride, carbonyl, trialkyl or triaryl phosphines, diphosphines, cyclopentadienyls, 2,4-alkanedionates, and mixtures thereof.

In some embodiments of the disclosure, the reaction is performed at a temperature within the range of about 45° C. to about 85° C. and a pressure within the range of about 30 to about 400 psig. In some such embodiments, the pressure may be from about 50 to 400 psig. In some such embodiments, the pressure may be from about 55 to 400 psig.

In some embodiments of the disclosure, the catalyst system also comprises a monophosphine compound. In some embodiments of the disclosure, the monophosphine compound is triphenylphosphine.

In some embodiments of the disclosure, the concentration of carbon monoxide in the liquid phase is maintained above 4 mmols/liter.

In some embodiments of the disclosure, the process further comprises hydrogenating the 4-hydroxybutyraldehyde in the presence of a hydrogenation catalyst to form 1,4-butanediol. In some embodiments of the disclosure, the hydrogenation catalyst is a nickel catalyst.

The present disclosure also provides a process to produce 4-hydroxybutyraldehyde by reacting allyl alcohol with carbon monoxide and hydrogen in the presence of a solvent and a catalyst system that includes a rhodium complex and a compound having the chemical structure of:

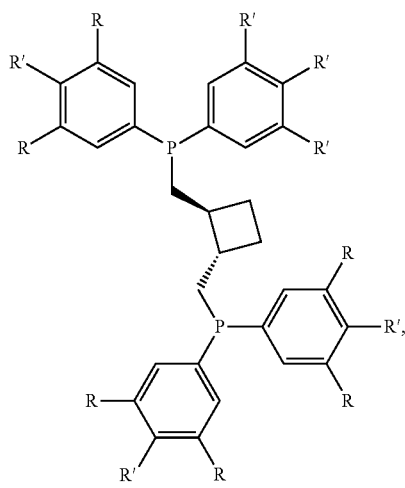

wherein R and R' are each independently selected from the group consisting of: methyl, ethyl, propyl, fluorinated methyl, fluorinated ethyl, or fluorinated propyl.

In some embodiments of the disclosure, the compound is trans-1,2-bis(bis(3,4,5-trimethylphenyl)phosphinomethyl)cyclobutane. In some embodiments of the disclosure, the compound is trans-1,2-bis(bis(3,4,5-triethylphenyl)phosphinomethyl) cyclobutane. In some embodiments of the disclosure, the reaction is performed at a temperature within the range of about 45° C. to about 85° C. and a pressure within the range of about 30 to about 400 psig. In some such embodiments, the pressure may be from about 50 to 400 psig. In some such embodiments, the pressure may be from about 55 to 400 psig. In some embodiments of the disclosure, the solvent is selected from the group consisting of $C_5$-$C_{20}$ aliphatic hydrocarbons, $C_6$-$C_{12}$ aromatic hydrocarbons, ethers, alcohols, and mixtures thereof. In some embodiments of the disclosure, the concentration of carbon monoxide in the liquid phase is maintained above 4 mmols/liter.

As used herein, the phrase "linear-to-branched ratio" or "L:B ratio" refers to the ratio of the linear HBA product to the branched HMPA product in the hydroformylation reaction.

As used herein, the term "Ligand A1" refers to trans-1,2-bis(bis(3,4,5-tri-n-alkylphenyl)phosphinomethyl)cyclobutane, wherein the n-alkyl can be methyl, ethyl, propyl, fluorinated methyl, fluorinated ethyl, or fluorinated propyl.

As used herein, the term "Ligand A2" refers to trans-1,2-bis(bis(3,5-di-n-alkylphenyl)phosphinomethyl)cyclobutane, wherein the n-alkyl can be methyl, ethyl, or propyl.

As used herein, the term "Ligand A3" refers to 2,3-O-isopropylidene-2,3-dihydroxy-1,4-bis[bis(3,5-dimethylphenyl)phosphino]butane.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
|---|---|
| BDO | 1,4-butanediol |
| DIOP | 2,3-O-isopropylidene-2,3-dihydroxy-1,4-bis(diphenylphosphino)butane |
| HBA | 4-hydroxybutyraldehyde |
| HMPA | 3-hydroxy-2-methylpropionaldehyde |
| Ligand A1 | trans-1,2-bis(bis(3,4,5-tri-n-alkylphenyl)phosphinomethyl)cyclobutane |
| Ligand A2 | trans-1,2-bis(bis(3,5-dimethylphenyl)phosphinomethyl)cyclobutane |
| Ligand A3 | 2,3-O-isopropylidene-2,3-dihydroxy-1,4-bis[bis(3,5-dimethylphenyl)phosphino]butane |
| MPD | 1,3-methyl propanediol |

BRIEF DESCRIPTION OF DRAWINGS

The FIGURE shows the four diphosphines prepared in this disclosure. Diphosphine 1A: Ligand A1; Diphosphine 1B: Ligand A2; Diphosphine 1C: Ligand A3; Diphosphine 1D: DIOP.

DETAILED DESCRIPTION

In one aspect of this disclosure, a compound having the following chemical structure is disclosed:

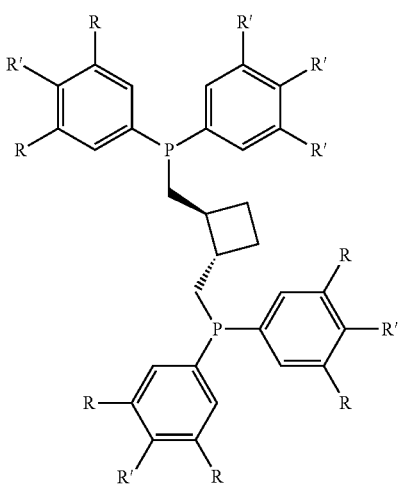

wherein both R and R' could be methyl, ethyl, propyl, fluorinated methyl, fluorinated ethyl, or fluorinated propyl. The fluorinated methyl group can be fluoromethyl, difluoromethyl, or trifluoromethyl.

In another aspect of this disclosure, a process to produce 4-hydroxybutyraldehyde is disclosed. The process comprises the step of reacting allyl alcohol with carbon monoxide and hydrogen in the presence of a solvent and a catalyst system comprising a rhodium complex and a trans-1,2-bis(bis(3,4,5-tri-n-alkylphenyl)phosphinomethyl)cyclobutane.

The catalyst system of the present disclosure may comprise a rhodium complex. Suitable rhodium complexes contain rhodium attached to ligand groups. The rhodium complex may be soluble in the solvent. There are no particular restrictions regarding the choice of ligands attached to the rhodium complex. For example, suitable ligands include hydrides, carbonyl, substituted and unsubstituted cyclopentadienyls, 2,4-alkanedionates, trialkyl or triaryl phosphines, diphosphines, and mixtures thereof. In some embodiments, the ligand(s) may include one or more of: a carbonyl, acetylacetonate (2,4-pentanedionate), triphenylphosphine, and mixtures thereof. Examples of rhodium complexes according to the present disclosure include (acetylacetonato) dicarbonylrhodium and tris(triphenylphosphine)rhodium carbonyl hydride.

The rhodium complex can be pre-associated with the trans-1,2-bis(bis(3,4,5-tri-n-alkyl-phenyl)phosphinomethyl) cyclobutane prior to use in the hydroformylation reaction such that the bis(bis(3,4,5-tri-n-alkylphenyl)-phosphinomethyl)cyclobutane ligand forms part of the rhodium complex, or it can be added separately. However, it is preferable to add the rhodium complex separate from the trans-1,2-bis (bis(3,4,5-tri-n-alkylphenyl)phosphinomethyl)-cyclobutane. The molar ratio of the trans-1,2-bis(bis(3,4,5-tri-n-alkylphenyl)-phosphinomethyl)cyclobutane:rhodium complex is in the range of 0.5:1 to 5:1. In some embodiments, the molar ratio of the trans-1,2-bis(bis(3,4,5-tri-n-alkylphenyl)-phosphinomethyl)cyclobutane:rhodium complex is in the range of 0.8:1 to 3:1. In some embodiments, the molar ratio of the trans-1,2-bis(bis(3,4,5-tri-n-alkylphenyl)-phosphinomethyl) cyclobutane:rhodium complex is in the range of 1:1 to 2:1.

In some embodiments, the catalyst system may additionally comprise a monophosphine compound. The monophosphine compound is in addition to any phosphine ligand that may be associated with the rhodium complex. The monophosphine compound is a trisubstituted phosphine that is represented by the formula:

$(R^1)_3P$ wherein $R^1$ is an aryl or alkyl group. Aliphatic $R^1$ groups may include methyl, ethyl, n-butyl, sec-butyl, octyl, and decyl. Aromatic $R^1$ groups may include phenyl, tolyl, and naphthyl. The $R^1$ groups may be the same or are different, but preferably are the same. In some embodiments, the monophosphine is a trisubstituted aryl phosphine. In other embodiments, the monophosphine is triphenylphosphine or tritolylphosphine.

A reaction solvent may be used in the practice of the process provided in this disclosure. Such reaction solvents may include those capable of solubilizing the rhodium complex and that are not reactive to the hydroxyaldehydes produced in the hydroformylation step. The reaction solvent may include any organic solvent having very low or minimal solubility in water. Such solvents may include $C_5$-$C_{20}$ aliphatic hydrocarbons, $C_6$-$C_{20}$ aromatic hydrocarbons, alcohols, ethers, and mixtures thereof. In some embodiments, the solvent may include toluene, cyclohexane, methyl t-butyl ether, and mixtures thereof.

Typical reaction conditions for the hydroformylation step are mild to favor the formation of the linear 4-hydroxybutyraldehyde (HBA) rather than branched 3-hydroxy-2-methylpropionaldehyde (HMPA) reaction product. Reaction temperature and pressure conditions may fall in the range of from about 20 to 120° C. and from about 20 to 600 psig. In some embodiments, the reaction temperature may be from about 45 to 85° C. and the reaction pressure may be from about 30 to 400 psig. In some such embodiments, the pressure may be from about 50 to 400 psig. In some such embodiments, the pressure may be from about 55 to 400 psig. In some embodiments, the reaction temperature may be from about 50 to 80° C. and the reaction pressure may be from about 40 to 300 psig. In some such embodiments, the pressure may be from about 50 to 400 psig. In some such embodiments, the pressure may be from about 55 to 400 psig. The molar ratio of $CO:H_2$ may be about 1:1, although the ratio can vary considerably. In some embodiments, the molar ratio of $CO:H_2$ may be from about 3:1 to about 1:3. In some embodiments, the molar ratio of $CO:H_2$ may be from about 2:1 to about 1:2. In some embodiments, the molar ratio of $CO:H_2$ may be from about 1.5:1 to about 1:1.5. The partial pressure of CO is typically within the range of 5 to 100 psig. The partial pressure of hydrogen is typically within the range of 40 to 200 psig. The reaction is conducted at these conditions until a predominance of the allyl alcohol has reacted, e.g. 60 to 99.9%, the products being largely 4-hydroxybutyraldehyde with some branched reaction products. The reaction time may take any amount of time; however, in some embodiments of the disclosure the reaction time is from 0.5 to 4 hours.

In some embodiments of the disclosure, the allyl alcohol starting concentration on a reaction solvent to feed basis is in the range of about 5 to 40 percent by weight in the solvent. In some embodiments, a lower concentration in the range of 5 to 10 percent by weight may be used.

In some embodiments of the disclosure, the hydroformylation of allyl alcohol is carried out such that the concentration of CO in the liquid phase ($[CO]_{liq}$) is maintained above 4 mmols/liter (0.004 M) during the hydroformylation. The value of $[CO]_{liq}$ is defined in U.S. Pat. No. 6,225,509, the teachings of which are incorporated herein by reference. In some embodiments of the disclosure, the liquid phase hydrogen:carbon monoxide molar ratio is in the range of from 10:1 to about 1:2. In some embodiments of the disclosure, the liquid phase hydrogen:carbon monoxide molar ratio is in the range of from 5:1 to about 1:2.

Following the hydroformylation step, the HBA product may be separated from the solvent and catalyst system by, for example, water extraction in an extraction vessel. Water extraction methods are well known in the art and can be effected by any suitable means, such as mixer-settlers, packed or trayed extraction columns, rotating disk contactors, or passed to a settling tank for resolution of the mixture into aqueous and organic phases. HBA, and any HMPA, remain soluble in the water (aqueous) phase and is separated from the solvent (organic) phase.

The 4-hydroxybutyraldehyde (and any 3-hydroxy-2-methylpropionaldehyde) reaction product may be subjected to an additional step of hydrogenating the 4-hydroxybutyraldehyde in the presence of a hydrogenation catalyst to produce 1,4-butanediol (BDO). Hydrogen may be added to the reaction vessel for the hydrogenation. Suitable hydrogenation catalysts may include any Group VIII metal, such as: nickel, cobalt, ruthenium, platinum, and palladium, as well as copper, zinc and chromium and mixtures and alloys thereof. In some embodiments, nickel catalysts may be used. In some embodiments, Raney®-type nickel and fixed bed nickel catalysts may be employed.

The hydrogenation reaction temperature and pressure conditions may be in the range of from about 60 to 200° C. and from about 200 to 1000 psig. In some embodiments, the hydrogenation reaction temperature and pressure conditions may be in the range of from about 80 to 140° C. and 300 to 1000 psig. Reaction time may fall in the range of from about 1 to 10 hours. During the hydrogenation reaction, BDO and MPD are formed while the high ratio of linear to branched products is substantially retained, along with other low co-product/byproducts.

The following examples merely illustrate certain embodiments of the disclosure. Those skilled in the art will recognize many variations that are within the spirit of the disclosure and scope of the claims.

Example 1: Preparation of Diphosphines

Four diphosphines were prepared to compare their catalytic capability in the production of 4-hydroxybutyraldehyde in terms of the linear:branch ratio and the overall yield.

Diphosphines 1A and 1B of the following general formula were prepared as described below.

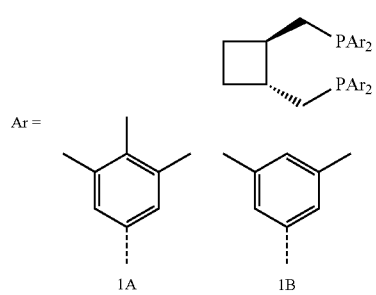

The synthesis of diphosphines 1A and 1B generally follows the reaction:

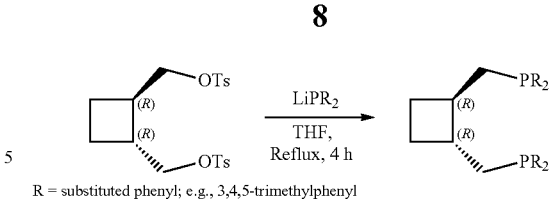

R = substituted phenyl; e.g., 3,4,5-trimethylphenyl

A solution of trans-1,2-cyclobutanedimethanol, bis(toluenesulfonate) in dry/degassed THF (1 equivalent, 1.73 g, $3.7 \times 10^{-3}$ moles of the dioxolane in 50 mL THF) was added drop-wise under argon to a solution of the appropriate lithium diarylphosphine (see formulae above) in dry/degassed THF (2.3 equivalents in 100 mL THF). The mixture was heated at reflux for 2 hours, then cooled, and the solvent removed under reduced pressure. The remaining solids were re-dissolved in dichloromethane, filtered through a silica bed, and the solvent removed under reduced pressure to yield the trans-1,2-bis(diarylphosphinomethyl)cyclobutane.

Diphosphine 1A: trans-1,2-bis(bis(3,4,5-trimethylphenyl) phosphinomethyl) cyclobutane.

Comparative Diphosphine 1B: trans-1,2-bis(bis(3,5-dimethylphenyl) phosphinomethyl)cyclobutane.

Comparative diphosphine 1C and 1D: Diphosphines 1C and 1D of the following general formula are prepared as described below.

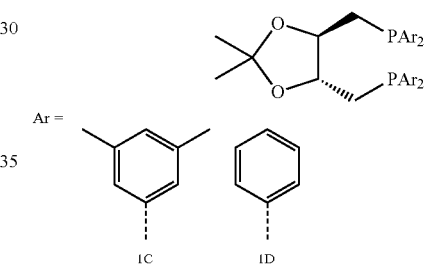

A solution of 2,2-dimethyl-4,5-bis[(toluenesulfonyloxymethyl)methyl]-1,3-dioxolane in dry/degassed THF (1 equivalent, 1.73 g, $3.7 \times 10^{-3}$ moles of the dioxolane in 50 mL THF) was added drop-wise under argon to a solution of the appropriate lithium diarylphosphine (see formulae above) in dry/degassed THF (2.3 equivalents in 100 mL THF). The mixture was heated at reflux for 2 hours, then cooled, and the solvent removed under reduced pressure. The remaining solids were re-dissolved in dichloromethane, filtered through a silica bed, and the solvent removed under reduced pressure to yield the 2,3-O-isopropylidene-2,3-dihydroxy-1,4-bis(diarylphosphino)butane.

Comparative Diphosphine 1C: 2,3-O-isopropylidene-2,3-dihydroxy-1,4-bis[bis(3,5-dimethylphenyl)phosphino]butane.

Comparative Diphosphine 1D: 2,3-O-isopropylidene-2,3-dihydroxy-1,4-bis[bis(phenyl)phosphino], known as DIOP.

Diphosphines 1A-1D are shown in the FIGURE.

Example 2: Hydroformylation Reaction Using Diphosphines

Allyl alcohol is hydroformylated using diphosphines 1A-1D according to the following procedure:

A solution of the desired diphosphine (2 equivalents or $8.6 \times 10^{-5}$ moles) in dry degassed toluene (15 g) was added to [Rh(CO)$_2$(acac)] (1 equivalent or $4.3 \times 10^5$ moles) in a 50 mL Parr autoclave. The solution was flushed three times with a 1:1 $CO/H_2$ mixture and then pressurized to 180 psig with the $CO/H_2$ mixture. The autoclave was then heated to 65° C. with stirring, allyl alcohol (3.5 mL) was injected, and the autoclave was pressurized to 200 psig with the $CO/H_2$ mixture. The autoclave was kept at a constant pressure of 200 psig, and the gas uptake of the reaction was monitored. When there was no further gas uptake, the autoclave was cooled and depressurized. The resulting solution was analyzed by gas chromatography to determine the products of the reaction. The reaction produces HBA, HMPA, and $C_3$ products (n-propanol and propionaldehyde).

The results are shown in Table 1 below. The results demonstrate that among the diphosphines, trans-1,2-bis(bis (3,4,5-tri-n-alkylphenyl)phosphinomethyl)cyclobutanes of this disclosure increase the linear HBA-to-branched HMPA (L:B) ratio above 11:1, whereas the best of the other diphosphines result in a L:B ratio of 10.0:1. In other words, ligand A1 of this disclosure enables a L:B ratio higher than the comparative diphosphines.

TABLE 1

Ligand comparison in hydroformylation of allyl alcohol.

|  | DIOP | Ligand A3 | Ligand A2 | Ligand A1 |
| --- | --- | --- | --- | --- |
| BDO | 85% | 88% | 90% | 91.6% |
| MPDiol | 14% | 11% | 9% | 8.2% |
| C3 | 1% | 1% | 1% | 0.2% |
| L:B | 6.1:1 | 8.0:1 | 10.0:1 | 11.2:1 |

Scale Up

Hydroformylation of allyl alcohol experiments were conducted in a continuous integrated pilot plant having hydroformylation, aqueous extraction, and hydrogenation stages under high pressure conditions using the Rh-Ligand A1 catalyst system. The pilot plant experiment conditions were as follows: 63° C. (145° F.) at 135 psig, with allyl alcohol feed concentration of 11%, (feed rate=80 cc/hr); [Rh], 160-190 ppm; (Ligand A1:Rh=(1.5-2):1). A comparative run using Rh-Ligand A2 was also performed. The results are summarized in the Table 2.

TABLE 2

Continuous hydroformylation comparison Ligands A1 and A2 at 135 psig.

| | Hydroformylation results | | Hydrogenation Results | | |
| --- | --- | --- | --- | --- | --- |
| Ligand | [Rh] (ppm) | Ligand concentration (ppm) | C$_3$ Sel (Wt %) | BDO Sel (%) | MPDiol Sel (%) | L:B Ratio BDO/ MPDiol |
| Ligand A2 | 170.5 | 0.1597 | 0.63 | 89.57 | 8.59 | 10.4:1 |
| Ligand A1 | 180.6 | 0.1553 | 0.72 | 90.14 | 8.15 | 11.06:1 |

The results showed a ~5% increase in L:B or BDO to MPDiol ratio, or from 10.4 to more than 11 after hydrogenation.

A low pressure continuous run was also conducted using the continuous integrated pilot plant at 63° C. (145° F.) and 50 psig, with allyl alcohol feed concentration of 18%, (feed rate=140 cc/hr); [Rh], 150-200 ppm; (Ligand A1:Rh=(1.5-2): 1. A comparative run using Rh-Ligand A2 was also performed. The results are summarized in Table 3.

TABLE 3

Continuous hydroformylation comparison Ligands A1 and A2 at 50 psig.

| | Hydroformylation results | | Hydrogenation Results | | |
| --- | --- | --- | --- | --- | --- |
| Ligand | [Rh] (ppm) | Ligand concentration (ppm) | C$_3$ Sel (Wt %) | BDO Sel (%) | MPDiol Sel (%) | L:B Ratio BDO/ MPDiol |
| Ligand A2 | 163 | 0.2014 | 0.74 | 88.5 | 9.36 | 9.46:1 |
| Ligand A1 | 154 | 0.1908 | 0.74 | 88.88 | 8.96 | 9.92:1 |

With the use of the Ligand A1, the yield of BDO improves from 85% to 91.6%. In terms of the linear-to-branch ratio (L:B), using the Ligand A1 can increase the L:B ratio to at least 10:1, and more preferably, at least 11:1.

The high- and low-pressure results in the continuous hydroformylation process again confirm that Ligand A1 exhibits superior linear-to-branched selectivity and overall yield to comparative Ligand A2. As expected, other diphosphines like DIOP, Ligand A3 and Ligand A2 have all been demonstrated on commercial scale with expected performance on continuous pilot unit scale.

In some embodiments of the disclosure, the L:B ratio may be greater than 10.5:1. In some embodiments of the disclosure, the L:B ratio may be greater than 11:1. In some embodiments of the disclosure, the L:B ratio may be greater than 12:1. In some embodiments of the disclosure, the L:B ratio may be in the range of from 9:1 to 12:1. In some embodiments of the disclosure, the L:B ratio may be in the range of from 10:1 to 11:6. In some embodiments of the disclosure, the L:B ratio may be in the range of from 10.1:1 to 11.2:1. In some embodiments of the disclosure, the L:B ratio may be in the range of from 10.45:1 to 11.2:1. In some embodiments of the disclosure, the L:B ratio may be in the range of from 10.5:1 to 12:1. In some embodiments of the disclosure, the L:B ratio may be in the range of from 11:1 to 11.2:1. In some embodiments of the disclosure, the L:B ratio may be in the range of from 10.9:1 to 11.2:1.

In some embodiments of the disclosure, the use, at high pressure, of a ligand having a 4' position constituent (e.g., Ligand A1) increased L:B ratio by about 12% compared to the use of a ligand without a 4' position constituent (e.g., Ligand A2). In some such embodiments using a ligand having a 4' position constituent, the selectivity of BDO increased by about 2% while decreasing MPDiol selectivity by about 9% compared to a ligand without 4' position constituent. In some embodiments of the disclosure, the L:B ratio increase may be from about 6% to about 18%. In some embodiments of the disclosure, the L:B ratio increase may be from about 9% to about 15%. In some embodiments of the disclosure, the L:B ratio increase may be from about 11% to about 13%. In some embodiments of the disclosure, the selectivity increase of BDO may be from about 1% to about 5% with a concomitant decrease in MPDiol selectivity of from about 4% to about 14%. In some embodiments of the disclosure, the selectivity increase of BDO may be from about 1% to about 3.5% with a concomitant decrease in MPDiol selectivity of from about 7% to about 11%. In some embodiments of the disclosure, the selectivity increase of BDO may be from about 1.5% to about 3% with a concomitant decrease in MPDiol selectivity of from about 8% to about 10%.

In some embodiments of the disclosure, the use, at low pressure, of a ligand without a 4' position constituent (e.g., Ligand A2) resulted in about an increase in L:B ratio of about 4.2% compared to the use of a ligand with a 4' position constituent (e.g., Ligand A1). In some such embodiments, however, the use of the ligand having a 4' position constituent still increased the selectivity of BDO by about 1% with negligible change in the selectivity to MPDiol compared to the ligand without 4' position constituent. In some embodiments of the disclosure, the L:B ratio increase may be from about 2% to about 6%. In some embodiments of the disclosure, the L:B ratio increase may be from about 3% to about 5%. In some embodiments of the disclosure, the L:B ratio increase may be from about 3.5% to about 4.5%. In some embodiments of the disclosure, the selectivity increase of BDO may be from about 0.25% to about 1.5%. In some embodiments of the disclosure, the selectivity increase of BDO may be from about 0.5% to about 1.25%. In some embodiments of the disclosure, the selectivity increase of BDO may be from about 0.75% to about 1.25%. In some embodiments, the selectivity increase of BDO may be accompanied by a negligible change in the selectivity to MPDiol.

As shown above, increasing pressure while using a ligand with a 4' position constituent, such as Ligand A1, improves L:B ratio and BDO selectivity while reducing MPDiol selectivity compared to the use of a ligand without a 4' position constituent, such as Ligand A2.

The following references are incorporated by reference in their entirety for all purposes.
U.S. Pat. No. 7,279,606
U.S. Pat. No. 7,271,295

What is claimed is:
1. A compound having the chemical structure of:

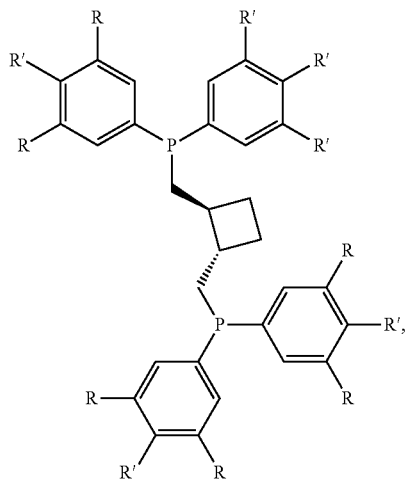

wherein R and R' are each independently selected from the group consisting of: methyl, ethyl, propyl, fluorinated methyl, fluorinated ethyl, or fluorinated propyl.

2. The compound of claim 1, wherein at least one fluorinated methyl is selected from the group consisting of: fluoromethyl, difluoromethyl, or trifluoromethyl.

3. A process to produce 4-hydroxybutyraldehyde comprising reacting allyl alcohol with carbon monoxide and hydrogen in the presence of a solvent and a catalyst system comprising a rhodium complex and a trans-1,2-bis(3,4,5-tri-n-alkylphenylphosphinomethyl)cyclobutane.

4. The process of claim 3, wherein the catalyst system comprises the rhodium complex and trans-1,2-bis(bis(3,4,5-trimethylphenyl)phosphinomethyl)cyclobutane.

5. The process of claim 3, wherein the catalyst system comprises the rhodium complex and trans-1,2-bis(bis(3,4,5-triethylphenyl)phosphinomethyl)cyclobutane.

6. The process of claim 3, wherein the solvent is selected from the group consisting of $C_5$-$C_{20}$ aliphatic hydrocarbons, $C_6$-$C_{12}$ aromatic hydrocarbons, ethers, alcohols, and mixtures thereof.

7. The process of claim 3, wherein the solvent is selected from the group consisting of toluene, cyclohexane, methylcyclohexane, methyl t-butyl ether, and mixtures thereof.

8. The process of claim 3, wherein the rhodium complex comprises rhodium and ligands selected from the group consisting of hydride, carbonyl, trialkyl or triaryl phosphines, diphosphines, cyclopentadienyls, 2,4-alkanedionates, and mixtures thereof.

9. The process of claim 3, wherein the reaction is performed at a temperature within the range of about 45° C. to about 85° C. and a pressure within the range of about 50 to about 400 psig.

10. The process of claim 3, wherein the catalyst system also comprises a monophosphine compound.

11. The process of claim 10, wherein the monophosphine compound is triphenylphosphine.

12. The process of claim 3, wherein the concentration of carbon monoxide in the liquid phase is maintained above 4 mmols/liter.

13. The process of claim 3, further comprising hydrogenating the 4-hydroxybutyraldehyde in the presence of a hydrogenation catalyst to form 1,4-butanediol.

14. The process of claim 13, wherein the hydrogenation catalyst is a nickel catalyst.

15. A process to produce 4-hydroxybutyraldehyde comprising reacting allyl alcohol with carbon monoxide and hydrogen in the presence of a solvent and a catalyst system comprising a rhodium complex and a compound having the chemical structure of:

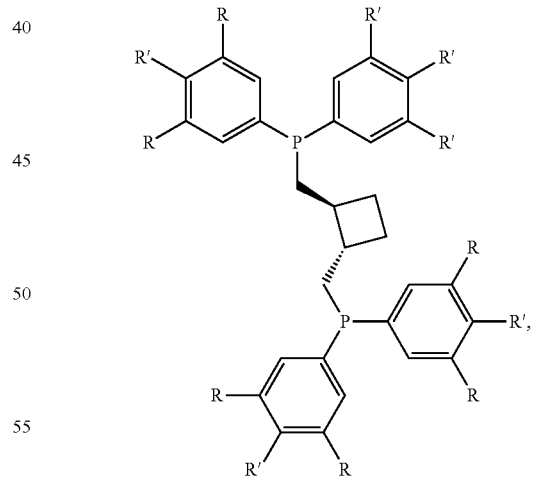

wherein R and R' are each independently selected from the group consisting of: methyl, ethyl, propyl, fluorinated methyl, fluorinated ethyl, or fluorinated propyl.

16. The process of claim 15, wherein the compound is trans-1,2-bis(bis(3,4,5-trimethylphenyl)phosphinomethyl)cyclobutane.

17. The process of claim 15, wherein the compound is trans-1,2-bis(bis(3,4,5-triethylphenyl)phosphinomethyl)cyclobutane.

18. The process of claim 15, wherein the reaction is performed at a temperature within the range of about 45° C. to about 85° C. and a pressure within the range of about 50 to about 400 psig.

19. The process of claim 15, wherein the solvent is selected from the group consisting of $C_5$-$C_{20}$ aliphatic hydrocarbons, $C_6$-$C_{12}$ aromatic hydrocarbons, ethers, alcohols, and mixtures thereof.

20. The process of claim 15, wherein the concentration of carbon monoxide in the liquid phase is maintained above 4 mmols/liter.

\* \* \* \* \*